United States Patent [19]

Nieuwenhuizen

[11] Patent Number: 5,124,439

[45] Date of Patent: Jun. 23, 1992

[54] ANTIBODIES AGAINST FIBRIN; IMMUNOGENIC PEPTIDES SUITABLE FOR PREPARING THE ANTIBODIES, METHOD FOR DETERMINING FIBRIN AND PHARMACEUTICAL PREPARATION BASED ON THE ANTIBODIES

[75] Inventor: Willem Nieuwenhuizen, Bunnik, Netherlands

[73] Assignee: Nederlandse Organisatie Voor Toegepast-Natuurwetenschappelijk Onderzoek Tno, The Hague, Netherlands

[21] Appl. No.: 516,428

[22] Filed: Apr. 30, 1990

[30] Foreign Application Priority Data

May 1, 1989 [NL] Netherlands ..................... 8901102

[51] Int. Cl.$^5$ ..................... C07K 15/28; A61K 39/00; A61K 39/395
[52] U.S. Cl. .................... 530/387.9; 424/88; 530/382; 530/388.25; 530/389.3
[58] Field of Search ................. 530/387, 382; 424/88

[56] References Cited

U.S. PATENT DOCUMENTS 4,916,070  4/1990  Matsueda et al. ............. 435/172.2

FOREIGN PATENT DOCUMENTS

3701812A1  8/1988  Fed. Rep. of Germany .

OTHER PUBLICATIONS

Fair et al. (1981) J. Biol. Chem. 256, 8018–8023.
Wilner et al. (1982) Biochemistry 21, 2687–2692.
Chung et al. (1983) Biochemistry 22, 3250–3256.
Houranieh et al. (1988) Hybridoma 7, 55–68.
Abstract 6480 from the FASEB Journal.

*Primary Examiner*—Robert A. Wax
*Assistant Examiner*—R. Keith Baker
*Attorney, Agent, or Firm*—Bachman & LaPointe

[57] ABSTRACT

Antibodies are provided which are directed against a sequence of amino acids corresponding to amino acids from the sequence 311–379 in particular 311–336 of the γ-chain of fibrinogen. These novel antibodies react specifically with fibrin, both type I and type II. They are effective in detecting, preventing and treating blood clot formation.

7 Claims, No Drawings

ANTIBODIES AGAINST FIBRIN; IMMUNOGENIC PEPTIDES SUITABLE FOR PREPARING THE ANTIBODIES, METHOD FOR DETERMINING FIBRIN AND PHARMACEUTICAL PREPARATION BASED ON THE ANTIBODIES

The invention relates to antibodies which react specifically with fibrin.

Thrombin consecutively detaches enzymatically the fibrinopeptides A of the Aα-chains and the fibrinopeptides of B of the Bβ-chains from the fibrinogen normally present in blood to form, respectively, monomeric fibrin type I and monomeric fibrin type II. Up to a certain concentration, there monomeric fibrins are able to remain in solution. At higher concentration, monomeric fibrin can polymerize to form a fibrin clot. To detect an imminent formation of a fibrin clot (thrombosis) early and to be able to prevent blood clots (thrombi) in the blood vessels, an early detection of fibrin in the blood is desirable, it being necessary for the means of detection to differentiate between the fibrinogen and the fibrin itself.

Said detection can in principle be carried out with the aid of antibodies against fibrin. Most of the antibodies against fibrin investigated are not, however, usable, because they also react with fibrinogen. Antibodies have also been described which do in fact differentiate between fibrin and fibrinogen. Thus, Kudryk et al. (Molecular Immunology 21, 89–94 (1984). EP-A 151,239) have described a monoclonal antibody which is induced by fibrin fragments as antigens and binds to the amino terminal end of the β-chain of fibrin. Hui et al. Hybridoma 5, 215–222 (1986)) have also described an antibody which is obtained by immunizing with a peptide of the β-chain termination of fibrin.

However, these antibodies have the disadvantage that they recognize only the amino terminal end of the β-chain of fibrin which is released on detaching the fibrinopeptide B, and they are therefore not usable for detecting fibrin I.

European Patent Application 152,612 describes a method for determining fibrin with the aid of an antibody which is induced by immunizing an animal with a peptide of the new amino terminal end of the α-chain which is produced by detaching fibrinopeptide A. In particular, the amino terminal end of the α-chain of fibrin is involved in this case.

International Patent Application WO 88,01514 describes an antibody against fibrin which is induced using human fibrin as an antigen. Said antibody is directed, in particular, against a section of the α-chain of fibrin.

Antibodies have now been found which act very specifically against fibrin and can be obtained by immunizing an animal with an immunogen which contains a section of the amino acid sequence of fibrin which is not active in fibrinogen but is active in fibrins type I and type II in immune reactions.

The antibodies according to the invention are characterized in that they are directed against a peptide having a sequence of 3–69 amino acid residues of which at least three are situated in the same relative position as the same amino acid residues in the amino acid sequence 311–379 starting from the N-terminal end of the γ-chain of fibrinogen and fibrin.

Preferably, 5 or more amino acid residues of the peptide are situated in the same relative position as the same amino chain residues in the amino acid sequence 311–369 of the γ-chain of fibrin. More preferably, 5 or more amino acid residues are situated in the same relative position as the same amino acid residues in the sequence γ-311–336 and, in particular, as the same amino acid residues in a smaller part of this sequence as 315–322.

The amino acid sequence γ-311–379 of fibrin is known and is represented by; (311) QFSTWDNDNDKFEGNCAEQDGSGWWM (336) NKCHAGHLNGVYYQGGTYSKASTPNGYDN-GIIWATWKTRWYSM(379). This amino acid sequence with a decoupling between N(336) and N(337) but with a disulphide bridge between C(326) and C(339) also occurs as fragment FCB-5 of the decomposition of fibrin with cyanogen bromide (see A. Henschen, Haemostaselogie 1 (1981), 49–61). Said FCB-5 can also be used for preparing antibodies according to the invention.

The immunogenic amino acid sequence can be prepared in a known manner, for example by a standard SPPS method such as is described by Stewart J. M., Young J. D. in "Solid Phase Peptide Synthesis", Pierce Chemical Company, 2nd impression, 1984. Under these circumstances, the side chains of amino acids which contain a functional group and should not participate in the coupling reaction are reversibly protected. The free carboxyl group of a derivatized amino acid is activated and therefore caused to react with the amino group of the derivatized amino acid to be coupled. This activation can be done with DCC (the abbreviations are explained below), DCC/HOBt or DCC/HONSu. The preference is for activation with DCC/HOBt.

Boc, Fmoc or Trt can be used as protective group for the α-amino function of amino acids.

The side chain functions as carboxyl, hydroxyl, guanidino and amino groups can be protected in accordance with their reactivity with the protective groups which are standard in peptide chemistry. Aliphatic or aromatic resides originating from alcohols such as methanol, tert-butanol or benzyl alcohol can be used as protection for the carboxyl groups in Asp and Glu. In this connection, tert-butanol is preferably. The hydroxyl group of Ser and Thr can also be protected by means of etherification with tert-butanol. The mercapto function of cysteine can be protected with the trityl group. The tosyl, nitro or Psm group, or protonation can be used to protect the guanidino function of Arg. The ε-amino group of Lys can be protected by means of the Boc or Msc group. In this case the Boc group is preferred. In view of the low stability towards bases of the protective group for the α-amino function (Fmoc), the binding of the first amino acid to the solid resin must be stable towards a base. The anchoring to the so-called p-alkoxybenzyl alcohol resin produces a labile ester binding in acid medium and this anchoring is preferred in this connection.

The optional "spacer", the section which links the end of a synthetic peptide to a carrier protein, can be assembled in various ways. The compounds suitable for this purpose have, for example, two identical or two different reactive groups at the ends of an alkyl group containing, for example, 2 to 8 carbon atoms. These groups include, inter alia, dialdehydes such as glutaraldehyde, diisocyanates such as 1,6-hexamethylene diisocyanate, diamines such as 1,6-hexamethylenediamine or ω-aminocarboxylic acids such as ε-aminocaproic acid, ε-maleimidocaproic acid. These bifunctional reagents are linked, possibly after activation, in a known manner to, on the one hand, the synthetic peptide and, on the other hand, the carrier protein. ε-Maleimidocaproic acid is preferred as a section of the total "spacer". The other section of the "spacer" may consist of a mercaptoacetyl group originating from acetylthioacetic acid and the amino acid norleucine (Nle) which does not occur in nature.

To introduce the "spacer", the protected peptide is acylated with Nle and acetylthioacetic acid while it is still bonded to the resin.

The ε-maleimidocaproic acid is activated by means of HONSu and DCC to form maleimidohexanoyl-N-hydroxysuccimide. After a carrier protein has been added, the active ester molecules are aminolyzed by the free amino groups of the carrier protein.

After detachment from the resin, deprotection and purification of the peptide extended with a section of the "spacer", the amino-terminal part is deprotected, for example by treatment with a mixture of 4N NaOH/methanol/dioxane (1/5/14) as a result of which the acetyl group is detached. The coupling between the carrier protein provided with a maleimido group and the synthesized protein extended with a mercaptoacetyl group proceeds spontaneously.

In principle, any protein, for example bovine serum albumin (BSA), but also other suitable organic or inorganic materials, can be used as carrier.

With the immunogen obtained this way, it is possible to immunize experimental animals such as mice, rats, rabbits or goats in the known manner. In this way, antisera containing polyclonal antibodies are obtained.

Preferably, monoclonal antibodies are induced in a corresponding manner, such as in accordance with Kohler, G., Milstein, C., Nature 256 (1975), 495-497. For this purpose, the known mouse myeloma cell lines can be used. Favorable results are obtained by using a cell line which does not itself produce any immunoglobulin.

Spleen cells from immunized Balb/c mice are fused with a myeloma cell line (preferably the cell line Sp 2/0 AG14 or P3×63 Ag 8653) which does not produce any immunoglobulin. The fused cells are selected by culturing in a selection medium in which unfused spleen cells and myeloma cells die and in which only spleen cells which are fused with the myeloma cells (hydridoma cells) survive. After this selection step, the hybridoma cells which produce the fibrin specific antibodies are selected in an ELISA system. The hybridoma cells which produce fibrin-specific antibodies are introduced into the abdominal cavity of Balb/c mice where they grow and produce ascites fluid which can be tapped off and which serves as a source for purifying the required monoclonal antibodies.

The invention also relates to an immunogen which can be used to prepare antibodies against fibrin as described above.

The antibodies according to the invention do not react with fibrinogen but do react with fibrin type I and type II. The sensitivity of this reaction is in the order of 0.1 μg/ml, which sensitivity is not limited by fibrinogen present in a 20,000-fold excess.

The advantage of determining fibrin type I is that the first step of all in the clotting is the formation of fibrin I. Because the determination of "soluble fibrin" is aimed precisely at detecting the very earliest clotting, a test directed at fibrin I has a better diagnostic value than one which is directed only at fibrin II. The formation of fibrin II proceeds via fibrin I.

A further advantage of the antibodies according to the invention is that they are directed against a site in the fibrin which is involved in accelerating the activation of plasminogen by t-PA (tissue plasminogen activator); i.e. in accelerated plasmin formation. Complexing of this site with the antibody will counteract that acceleration and thus help to keep the fibrin present in plasma intact during the determination thereof. This is impossible with the antibodies against fibrin hitherto known.

The invention therefore relates to a method for detecting and determining fibrin, in particular in blood, with the aid of an antibody as described above. This may take place, for example, with a so-called "Sandwich" ELISA or "Sandwich" EIA.

The purified monoclonal antibody is immobilized under these conditions on a solid carrier and is brought into contact in that condition with the liquid (blood/plasma) whose fibrin content it is desired to determine. Then the quantity of fibrin bound in this way be the monoclonal antibodies is determined by adding a second antibody which is labelled with a detectable label such as a radioactive atom, a fluorescent or luminescent group or, in particular, an enzyme (for example horseradish peroxidase (HRP)). The amount of the bound second antibody is then determined by measuring the activity, for example the enzyme activity of the label. Said activity is a measure of fibrin concentration in the blood or plasma used.

A possible embodiment of the method comprises detecting fibrins by using a second labelled antibody which recognizes another epitope of fibrin. In that case the monoclonal antibody described here can be used in immobilized form and the second as an HRP conjugate. Said second antibody may be a monoclonal antibody, but also a mixture of monoclonal antibodies or even a polyclonal antiserum. Although the first antibody, according to the invention, is already amply specific for fibrin, the specificity of the detection method is, if possible, still further improved by using a second antibody which also recognizes fibrin.

The invention further relates to a kit for determining fibrin which contains an antibody as described above, for example in an antiserum, and also further constituents needed to determine fibrin.

Because the antibodies according to the invention are fibrin-specific, they can also be used to detect and to localize fibrin (specifically, blood clots) in vivo. For this purpose the antibodies are labelled with a substance which can be detected outside the body. For example, this is $Tc^{99m}$ which can be detected because it is radioactive and emits (γ) radiation. The method described by Feitsma in Nucl. Med. Comm. 8 (1987), 771-777 is particularly suitable for this purpose. The fibrin specificity can also be used to direct an active substance, in particular a substance which is active in dissolving blood clots, to the site of the clots. As a result, higher efficiency is acquired for the active substance. A combination of tissue-type plasminogen activator or other plasminogen activators, plasminogen, plasmin or, other proteases with antifibrin antibodies comes to mind. Examples of this principle are described by M. S. Runge et al. Proc. Natl. Acad. Sci. 84 (1987), 7659-7662 and C. Bode et al. J. Biol. Chem. 262 (1987), 10819-10823.

The invention also relates to a pharmaceutical preparation that contain such an active substance coupled to an antibody as described above. Said active substance is preferably a thrombolytic agent. Examples of thrombolytics are tissue-type plasminogen activator (or variants thereof obtained via recombinant DNA techniques; the same for urine-type plasminogen activator (U-PA)), streptokinase, plasmin and plasminogen.

In the above and in the examples below, the abbreviations used have the following meanings:
Ata-OH: acetylthioacetic acid
BSA: bovine serum albumin
Boc: tert-butoxycarbonyl
Bu$^t$: tert-butyl
CCD: countercurrent distribution
DCC: dicyclohexylcarbodiimide
DMAP: 4-dimethylaminopyridine
DMF: dimethylformamide
Fmoc: 9-fluorenylmethyloxycarbonyl
HOBt: 1-hydroxy-1H-benzotriazole
HONSu: N-hydroxysuccinimide
MHS: 6-(maleimido)hexanoyl-N-hydroxysuccinimide
MSA: methanesulphonic acid
Msc: methylsulphonylethyloxycarbonyl
Nle: D,L-norleucine
(P): p-alkoxybenzyl alcohol resin
PBS: phosphate-buffered salt solution (pH=6.9, 0.15M NaCl)
Pms: pentamethylphenylsulphonyl
SPPS: solid phase peptide synthesis
Tha: mercaptoacetyl
TFA: trifluoroacetic acid
TLC: thin-layer chromatography
Trt: trityl

EXAMPLE I

The peptide γ-311-336 (QFSTWDNDNDKFEGN-CAEQDGSGWWM) was prepared on a p-alkoxybenzyl alcohol resin (Bachem, Bubendorf, Switzerland) with the aid of a semi-automatic peptide preparer (Labortec SP-640, Bubendorf, Switzerland). The amino acids were coupled in the sequence given as Fmoc amino acids according to a standard method, starting with the C-terminal methionine. In this process, the following protective groups were used for the side chains: [Lys(K): Boc; Cys(C): Trt; Glu(E), Asp(D), Thr(T), and Ser(S): Bu$^t$]. The amino acids were coupled by means of DCC/HOBt. The resin was finally deblocked and released by treatment by TFA/MSA/thioanisole (10/1/1) for 2 hours at room temperature, followed by filtration, precipitation with other and lyophilizing from water. The crude peptide was purified with the aid of CCD in an apparatus with elements of 10 ml of lower phase, supplied by Labortec, Bubendorf, Switzerland. Use was made of the butanol/acetic acid/water system (5/1/4). Samples from the maxima were hydrolyzed in 5.7N hydrochloric acid at 105° C. for 48 hours in sealed glass ampoules evacuated at −80° C. The hydrolyzate was evaporated down several times with water and subjected to amino acid analysis in a JEOL-JLC-6AM analyser.

EXAMPLE II

The peptide mercaptoacetyl-D,L-norleucylfibrinogen-γ (311-336) provided with a section of the "spacer" (according to Example I) was obtained in accordance with the synthesis scheme reproduced in European Patent Application 347,959.

After purification by means of CCD, the peptide was characterized by means of TLC and amino acid analysis. The norleucine was included in order to be able to determine the number of peptides per carrier molecule. The chemical purity was determined by means of TLC in various solute systems.

EXAMPLE III 4.5 mg of MHS were added to 50 mg of very pure BSA dissolved in 1 ml of phosphate buffer (pH=8). After reacting for 5 minutes, the reaction mixture was purified by means of gel filtration using Sephadex G-25 with phosphate buffer (pH=6) as eluent.

37 mg of the activated peptide from Example II were added to the BSA-spacer solution thus obtained. After reacting for 2 hours at room temperature, the reaction mixture was dialyzed against PBS and lyophilized.

EXAMPLE IV

Polyclonal antibodies

A monotonic, N-terminally coupled peptide carrier protein conjugate is dissolved in 0.15M NaCl and mixed with an equal volume of Freund's complete adjuvans. A volume of this mixture which corresponds to 125 μg of total protein (10 μg of coupled peptide) is injected into the abdominal cavity of Balb/c mice. These injections are repeated 4 times but Freund's incomplete adjuvans is now used.

The presence of antibodies in the blood of the mice immunized in this manner is determined by means of the ELISA described above.

EXAMPLE V

Monoclonal Antibodies

The Balb/c mice immunized according to Example IV are intravenously injected with 250 μg of BSA-peptide conjugate dissolved in 0.15M NaCl three days before the removal of their spleen. Spleen cells from the mice are mixed with myeloma cells in a ratio of 4:1 in the presence of 40% polyethylene glycol (molecular weight 4000) as described by Köhler and Milstein (Nature 256 (1975), 495-497). After fusion, the cell suspension is diluted and distributed over the wells of 4 microtiter plates so that each well contains $3.3 \times 10^5$ spleen cells.

After the spleen cells and the myeloma cells have died in the Köhler and Milstein selection medium, the culture liquids from the wells which exhibit hybridoma growth are tested after 10-14 days for the presence of fibrin-specific antibodies.

For this purpose, the wells of polystyrene microtiter plates are coated with fibrinogen or fibrin monomers (prepared according to Belitzer et al., Biochim. Biophys. Acta 154 (1968) 367). After washing, small volumes of the culture liquids of the hybridomas are introduced into the coated wells and incubated therein for 1 hour at 37° C. Then the wells are again washed. A solution of polyclonal antibodies directed against mouse immunoglobulins and coupled with horseradish peroxidase is then introduced into the wells and incubated therein for 1 hour at 37° C. After washing, the presence of peroxidase activity in the wells is determined and quantified as a measure of the amount and specificity of the monoclonal antibodies present in the culture liquids.

The cell lines which produce a fibrin-specific antibody are then cloned two more times as described by McKearn (T. J. McKearn in "Monoclonal Antibodies, Hybridomas: a new dimension in biological analysis, Plenum, New York, 1980, page 374).

Examples of two cell lines found in this way:

| antigen used | ELISA result | |
| --- | --- | --- |
| | cell line I | cell line II |
| fibrogen | 0.120 | 0.086 |
| fibrin monomer | 1.804 | 1.232 |

EXAMPLE VI

Determination of Fibrin in Blood

Fresh blood from healthy donors is treated for a short time with a small amount of thrombin. In this process, a quantity of soluble fibrin is produced in said plasma. A solution (10 μg/ml) of a monoclonal antibody (in 0.04M Tris/HCl, pH 7.5) prepared according to the invention is introduced into the wells of a polystyrene microtiter plate and incubated therein for 16 hours at 4° C. During this incubation, the monoclonal antibodies are adsorbed at the wall of the wells. After washing, dilution series of the plasma treated with thrombin and of the same plasma without thrombin treatment are pipetted into the wells. After incubating for 1 hour, preferably at 4° C., the wells are washed and a solution of a horseradish peroxidase conjugate with another monoclonal antibody (which does not need to be fibrin-specific) is introduced into the wells. After incubating again for 1 hour (preferably at 4° C.) the wells are washed and the peroxidase activity is used as a measure of the amount of fibrin which has been bound by the wells coated with the fibrin-specific antibody. This is done by using a mixture of tetramethylbenzidine and hydrogen peroxide as substrate for peroxidase (E. S. Bos et al. J. Immunoassay 2 (1981), page 187). As a result of the action or peroxidase a blue product is produced in this way which changes to yellow when the reaction is stopped by adding 1M $H_2SO_4$ after incubating for 10 minutes at 37° C. The intensity of the yellow color is measured at a wavelength of 405 m/u and is a measure of the peroxidase activity.

An example:

| | Optical density at 405 nm found for plasma dilution: | | | | |
| --- | --- | --- | --- | --- | --- |
| | 1/20 | 1/60 | 1/180 | 1/540 | 1/1620 |
| Untreated plasma | 0.20 | 0.10 | 0.08 | 0.08 | 0.08 |
| Plasma treated with thrombin | 1.86 | 1.12 | 0.64 | 0.34 | 0.20 |

I claim:

1. Antibodies which bind specifically with fibrin but not to fibrinogen, said antibodies being directed against a peptide consisting essentially of a sequence of 5 to 69 amino acid residue from the amino acid sequence 311-379 of the gamma-chain of fibrinogen.

2. Antibodies according to claim 1 which are directed against a peptide containing a sequence of 5 to 69 amino acid residues from the amino acid sequence 311-336 of the gamma-chain of fibrinogen.

3. Antibodies according to claim 2 directed against a peptide containing the amino acid sequence of gamma 311-379.

4. Antibodies according to claim 1 obtained by immunizing with an amino acid sequence which is linked to an immunogen carrier.

5. Antibodies according to claim 1 wherein the antibodies are monoclonal.

6. An immunogenic peptide consisting essentially of a sequence of 5 to 69 amino acid residues from the amino acid sequence 311-370 of the gamma-chain of fibrogen.

7. Antibodies according to claim 1 directed against a peptide containing the amino acid sequence gamma 315-322.

* * * * *